United States Patent [19]

McRae

[11] Patent Number: Plant 6,677

[45] Date of Patent: Mar. 21, 1989

[54] LILY PLANT NAMED "BOLERO"

[75] Inventor: Edward A. McRae, Boring, Oreg.

[73] Assignee: Melridge, Inc., Aurora, Oreg.

[21] Appl. No.: 926,714

[22] Filed: Nov. 4, 1986

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Charles W. Rummler

[57] ABSTRACT

A new variety of hybrid lily plant bearing large clusters of medium sized, upright flowers particularly characterized by their clear pink, cream-centered coloration and their unusually broad, copiously spotted tepals. The moderately tall stature of the plant, the excellent form and long persistence of its flowers and its relatively short leaves, along with its ability to be forced into flower out of season, make it especially suitable as a cut flower variety. The color pattern and silhouette of this plant are completely new in the upright Asiatic divisions of lilies suited to cut flower forcing and to mass commercial cultivation. This plant is highly resistant to disease and shows high tolerance of virus, making it an excellent garden plant, and the bulbs may be precooled and forced throughout the year for cut flower production. The clone is vigorous and is a good grower and propagator.

1 Drawing Sheet

BACKGROUND OF THE INVENTION

This new lily plant originated as a seedling selected from a group of seedlings planted by me at Sandy, Oreg., with seeds resulting from my crossing the clonal cultivar 'Peachblush' as the seed parent and the clonal cultivar 'Gypsy' as the pollen parent. This crossing was done with the object of producing lilies in shades of pink and peach well suited for forcing for cut flower production out of season, heretofore unknown in the lily breeding art.

This particular seedling was selected for propagation because of its flowers being characterized by clear pink and cream-throated coloration with a deeper stripe of pink along the tepal midrib, a color pattern unique in this type of lily. This selected plant was asexually reproduced by me at Sandy, Oreg., and under my direction successive generations of this plant were produced by bulb scale propagation and by natural propagation from bulblets; and this extended propagation of the new plant has demonstrated that the novel and distinctive characteristics of this plant hold true, under asexual propagation, from generation to generation and appear to be firmly fixed.

Continued work with this new variety shows that it remains moderately tall and is not overly susceptible to bud abortion when forced into flower out of season as a cut flower plant. In addition, the clone possesses to a high degree the desirable characteristics of hybrid vigor, great hardiness, and disease resistance. Thus the plant possesses all of the desirable characteristics of excellence of form, color and habit and the clone has been found to be a vigorous and good grower and propagator as observed at Sandy, Oreg.

The plant is also well suited to forcing out of season when the bulbs are dug at the appropriate time and properly precooled; October-dug bulbs, properly precooled and potted in January, will flower under glass in western Oregon with no supplemental lighting and at moderate greenhouse temperatures in an average of seventy to eighty-five days.

DESCRIPTION OF THE DRAWING

My new variety of lily plant is illustrated by the accompanying photographic drawing, which shows an open bloom in full color and illustrates the flower form and tepal arrangement, as well as its distinctive deep pink, cream-centered coloration with the deeper pink ray along the tepal midrib and the copious tepal spotting, the colors shown being as close to those specified herein as is reasonably possible to obtain by conventional photographic procedures.

DESCRIPTION OF THE NEW VARIETY

The following is a detailed description of my Asiatic hybrid lily variety with nomenclature according to The International Lily Register of The Royal Horticultural Society of London, England (Second Edition, 1969), and with color designations according to The R.H.S. Colour Chart published by the Society in 1966.

THE PLANT

Origin: Seedling.

Parentage:

*Seed parent.*—Lilium 'Peachblush' (U.S. Plant Pat. No. 4,334).

*Pollen parent.*—Lilium 'Gypsy' (unpatented).

Classification:

*Horticultural.*—Division I-A, Upright Asiatic Hybrid Lily, according to The Horticultural Classification of Lilies by The Royal Horticultural Society of London.

*Commercial.*—Asiatic Hybrid Lily.

Form: Single stem, erect and stately.

Height: About 90 to 125 cm. for stems produced by glasshouse forcing of bulbs having a circumference of from 15 to 18 cm., provided their light levels are adequate; low light levels may cause "stretching".

Growth: Vigorous and upright.

Foliage:

*Quantity.*—Abundant.

*Leaf size.*—About 7 to 10 cm. long and about 0.5 to 1 cm. wide.

*Leaf shape.*—Lanceolate with acute tip.
*Texture.*—Leathery.
*Aspect.*—Glossy and lightly pubescent.
*Color.*—Dark green; somewhat lighter on the lower side.

Bulbs:
*Size.*—Various, according to age, and ranging up to about 25 cm. in circumference in commercial use.
*Color.*—White.

THE BUD

Form: Long ovoid with rounded base and obtuse tip.
Size: About 8 to 9 cm. long and about 5 cm. in circumference just prior to opening.
Opening rate: The bud opens slowly, taking about one hour in response to morning light.
Color: Soft pink with flush of green along the midribs and at the tip, prior to opening and as the tepals begin to unfurl.
Peduncle:
*Length.*—Averages 4 to 6 cm. but may become longer if light levels are too low, or if bulbs have been improperly stored prior to forcing.
*Color.*—Dark green.

THE FLOWER

Blooming habit: Once annually and profusely in midseason for Asiatic lilies.
Size: Medium, averaging about 13 to 15 cm. in diameter.
Borne: As a single, compact, racemose inflorescence having 8 to 14 buds from a bulb about 12 to 16 cm. in circumference. The stem also produces secondary buds.
Shape: Cup-shaped upon first opening and becoming flatter as the tepals recurve by the second day.
Tepalage:
*Number.*—Six.
*Arrangement.*—Hexagonal and imbricated.
*Shape.*—Ovate and entire margins.
*Size.*—The outer tepals average about 2.5 to 3 cm. wide and the inner tepals average about 3.5 cm. wide. The inner tepals meet and slightly overlap.
*Appearance.*—Shiny.
*Color.*—The basic color is clear pink, 58C-D, overlaying a cream-colored throat, 8B-C, formed by a cream-yellow blush about 2 to 3 cm. wide at the base of each tepal parallel to the nectary. Also, there is a deeper pink flush of 58A-B, about 1 to 2 mm. wide, extending from the apex of the nectary furrow along the midrib of each tepal. The nectaries are very light cream to white and are pubescent.
*Tepal spotting.*—The tepals are copiously spotted with medium sized, dark magenta spots on the basal half of each tepal.

Pedicel:
*Length.*—From 4 to 8 cm., in average.
*Color.*—Dark green; lightly pubescent.
Color changes: The flowers may lighten slightly to 58D at the tips as the flowers age. Strong heat and light can reduce the pink pigmentation; but there is little change in flower color if light and temperature levels are suitable for cut flower maintenance.
Persistence: The tepals stay on the stems for about 3 weeks.
Fragrance: None.
Lasting quality: The flower is long lasting, both on the plant and as a cut flower.
Disease resistance: The flower and plant are resistant to disease; and in particular, they are resistant to Botrytis blight and Fusarium bulb rot, as observed in western Oregon.

THE REPRODUCTIVE ORGANS

Stamens:
*Number.*—Six.
*Arrangement.*—Typical of the genus Lilium.
*Pollen and dehisced anthers.*—183A to 180A.
*Filaments.*—Length: About 5 cm. Color: Soft cream, 18C, to pink, 36A.
Pistil:
*Number.*—One.
*Style.*—Length: About 5 cm.
*Stigma.*—Size: Medium. Color: Soft plum.
Character of ovary: Typical of genus Lilium.

THE FRUIT

Fertility: The fruit is fertile.
Shape: Ovoid.
Color at maturity: Soft brown, sometimes overlaid with soft plum.

This new lily variety most closely resembles 'Peachblush' but is distinguished by having pinker and less peach toned coloration, a lighter toned cream center and much more conspicuous spotting. This new plant also resembles the related variety 'Rhumba' (Ser. No. 926,715) but is lighter pink with a much smaller cream throat, much more conspicuous spotting, and a distinctive deeper ray along each tepal midrib.

I claim:

1. A new and distinct variety of Asiatic hybrid lily, substantially as herein shown and described, particularly characterized by its extremely broad tepalled, attractively spotted, cream-throated, clear pink flowers having a deeper pink stripe along the tepal midribs; its vigorous growth and rapid propagation; the excellence of its flower form; and its versatility both as a garden plant and as a cut flower variety suited to forcing into flower out of season from properly precooled bulbs.

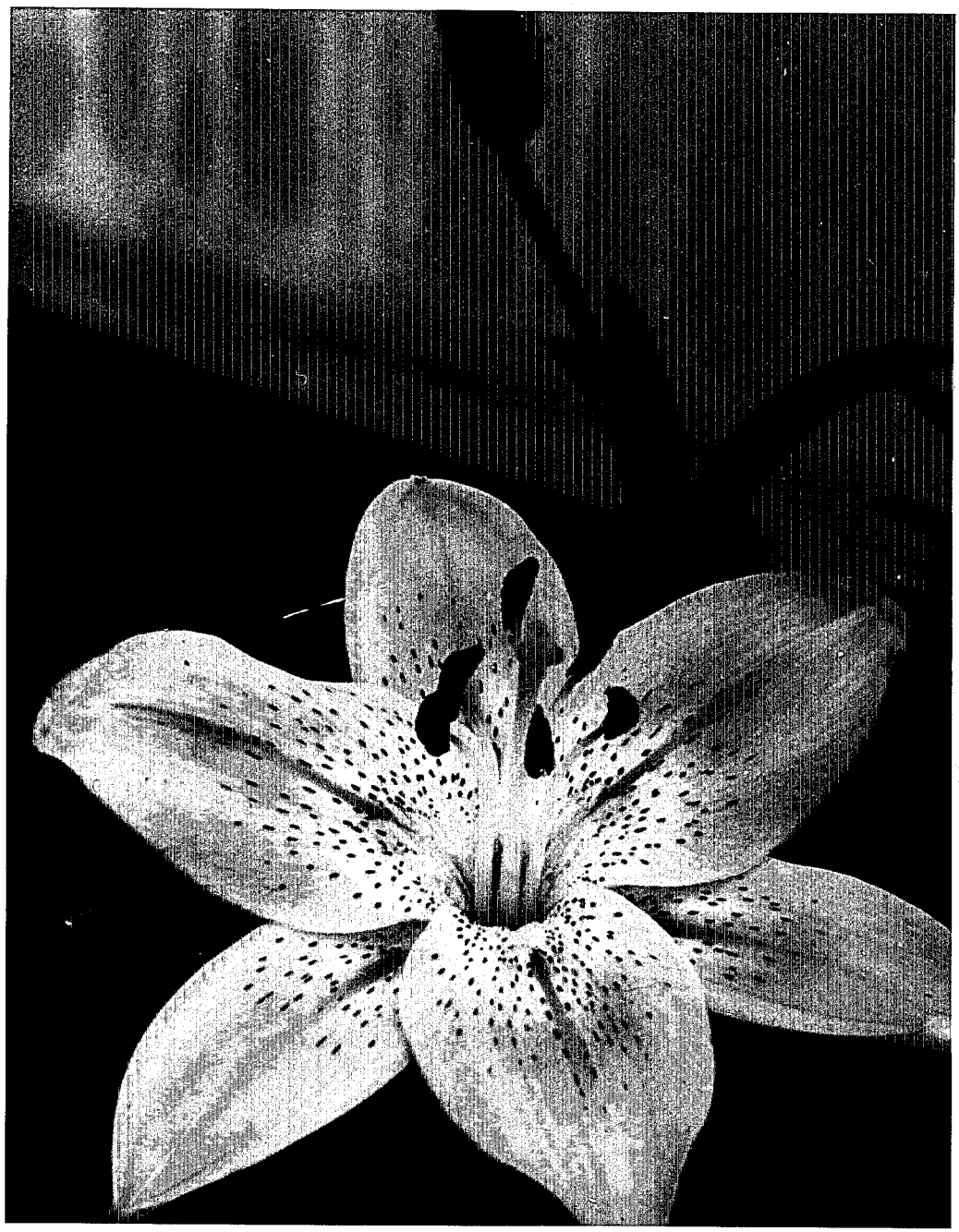

* * * * *